(12) United States Patent
Gerard et al.

(10) Patent No.: US 7,129,075 B2
(45) Date of Patent: Oct. 31, 2006

(54) ISOLATED CEL II ENDONUCLEASE

(75) Inventors: Gary F. Gerard, Frederick, MD (US);
Harini Shandilya, Bethesda, MD (US);
Peter Qiu, Gaithersburg, MD (US);
James M. D'Alessio, Middletown, MD (US)

(73) Assignee: Transgenomic, Inc., Omaha, NE (US)

( * ) Notice: Subject to any disclaimer, the term of this patent is extended or adjusted under 35 U.S.C. 154(b) by 353 days.

(21) Appl. No.: 10/688,665

(22) Filed: Oct. 17, 2003

(65) Prior Publication Data

US 2004/0166510 A1    Aug. 26, 2004

Related U.S. Application Data

(60) Provisional application No. 60/419,568, filed on Oct. 18, 2002.

(51) Int. Cl.
*C12N 9/22*    (2006.01)

(52) U.S. Cl. ...................................................... 435/199

(58) Field of Classification Search ..................... None
See application file for complete search history.

(56) References Cited

U.S. PATENT DOCUMENTS

| | | | |
|---|---|---|---|
| 5,868,245 A | 2/1999 | Alt | 206/210 |
| 5,869,245 A * | 2/1999 | Yeung | 435/6 |
| 6,027,898 A | 2/2000 | Gjerde et al. | 435/6 |
| 6,391,557 B1 * | 5/2002 | Yeung | 435/6 |
| 6,699,980 B1 * | 3/2004 | Yeung | 536/23.1 |

OTHER PUBLICATIONS

Colbert et al., "High-Throughput Screening for Induced Point Mutations", Plant Physiol. 2001 163:480-484.

Kulinski et al., "Modified Primers Facilitate Rapid Screening of 16S rRNA Gene Libraries", BioTechniques 2000 29(1):44-48.

Oleykowski et al., "Mutation detection using a novel plant endonuclease", Nucleic Acids Research 1998 26(20):4597-4602.

Sokurenko et al., "Detection of simple mutations and polymorphisms in large genomic regions", Nucleic Acids Research 2001 29(22e111):1-8.

Yang et al., "Purification, Cloning and Characterization of the CEL 1 Nuclease", Biochemistry 2000 39:3533-3541.

* cited by examiner

*Primary Examiner*—Charles L. Patterson, Jr.
(74) *Attorney, Agent, or Firm*—Licata & Tyrrell P.C.

(57) ABSTRACT

The present invention relates to the isolation and characterization of CEL I and CEL II endonuclease proteins. Methods and kits for identifying mismatches in double-stranded DNA are also provided.

9 Claims, 4 Drawing Sheets

SEQUENCE LISTING

<160> NUMBER OF SEQ ID NOS: 4

<210> SEQ ID NO 1
<211> LENGTH: 16
<212> TYPE: PRT
<213> ORGANISM: Apium graveolens

```
<220> FEATURE:
<221> NAME/KEY: MISC_FEATURE
<222> LOCATION: (1)..(2)
<223> OTHER INFORMATION: "Xaa" represents any amino acid residue
<220> FEATURE:
<221> NAME/KEY: MISC_FEATURE
<222> LOCATION: (10)..(10)
<223> OTHER INFORMATION: "Xaa" represents any amino acid residue
<220> FEATURE:
<221> NAME/KEY: MISC_FEATURE
<222> LOCATION: (13)..(13)
<223> OTHER INFORMATION: "Xaa" represents any amino acid residue
<220> FEATURE:
<221> NAME/KEY: MISC_FEATURE
<222> LOCATION: (15)..(15)
<223> OTHER INFORMATION: "Xaa" represents any amino acid residue

<400> SEQUENCE: 1

Xaa Xaa Lys Gln Gly His Phe Ala Ile Xaa Lys Ile Xaa Gln Xaa Phe
1               5                   10                  15

<210> SEQ ID NO 2
<211> LENGTH: 9
<212> TYPE: PRT
<213> ORGANISM: Apium graveolens
<220> FEATURE:
<221> NAME/KEY: MISC_FEATURE
<222> LOCATION: (1)..(1)
<223> OTHER INFORMATION: "Xaa" represents any amino acid residue.
<220> FEATURE:
<221> NAME/KEY: MISC_FEATURE
<222> LOCATION: (4)..(4)
<223> OTHER INFORMATION: "Xaa" represents any amino acid residue.

<400> SEQUENCE: 2

Xaa Asn Asn Xaa Thr Glu Ala Leu Met
1               5

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 3
cgccaaagaa tgatctgcgg agctt                                         25

<210> SEQ ID NO 4
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 4
acacctgatc aagcctgttc atttgattac                                    30
```

ISOLATED CEL II ENDONUCLEASE

This application claims the benefit of priority from U.S. provisional application Ser. No. 60/419,568, filed on Oct. 18, 2002, whose contents is incorporated herein by reference in its entirety.

BACKGROUND OF THE INVENTION

A novel family of DNA mismatch-specific endonucleases from plants have been found (Oleykowski, et al. (1998) *Nucl. Acid Res.* 26:4597–4602; Yang, et al. (2000) *Biochem.* 39:3533–3541). Celery was found to be enriched in this endonuclease activity and the purified enzyme was accordingly named CEL I (Oleykowski, et al. (1998) supra; Yang, et al. (2000) supra). CEL I cleaves DNA at the 3'-side of sites of base-substitution mismatch and DNA distortion.

CEL I is useful in mismatch detection assays that rely on nicking and cleaving duplex DNA at insertion/deletion and base-substitution mismatches (Oleykowski, et al. (1998) supra; Yang, et al. (2000) supra; Kulinski, et al. (2000) *BioTechniques* 29:44–48; Colbert, et al. (20001) *Plant Physiol.* 126:480–484; Sokurenko, et al. (2001) *Nucl. Acids Res.* 29:e111; U.S. Pat. No. 5,869,245).

Purified preparations of CEL nuclease identified as CEL I contain two different protein species, CEL I and CEL II (Yang, et al. (2000) supra; U.S. Pat. No. 5,869,245). One species, called CEL I, has an apparent molecular weight of 43 kDa as determined by SDS-PAGE. Removal of N-linked oligosaccharides with Endo $H_f$ reduces the molecular weight to 29 kDa. CEL I was partially sequenced and the gene encoding CEL I was isolated from a celery cDNA library, sequenced, and cloned into *E. coli* (Yang, et al. (2000) supra; U.S. Pat. No. 5,869,245). CEL II has an apparent molecular weight of 39 kDa as determined by SDS-PAGE and removal of N-linked oligosaccharides reduces the molecular weight to 37 kDa. Chromatographic separation of CEL I and CEL II has not been described and isolated preparations of CEL I nuclease contain varying ratios of CEL I and CEL II enzymes.

The present invention relates to the isolation and characterization of CEL I and CEL II from preparations of CEL I nuclease mixtures of celery. CEL I and CEL II enzymes are differentiated in a DNase solubilization assay; CEL I prefers acidic conditions whereas CEL II prefers alkaline reaction conditions.

SUMMARY OF THE INVENTION

One aspect of the present invention is an isolated CEL II or CEL I endonuclease protein. Preferably, an isolated CEL II endonuclease is substantially free of CEL I endonuclease and an isolated CEL I endonuclease is substantially free of CEL II endonuclease.

Another aspect of the present invention is a method for preparing an isolated CEL I or CEL II endonuclease protein.

The method involves:

extracting proteins from a sample such as a plant (e.g., celery);

separating the proteins by concanavalin A affinity chromatography;

separating the product of concanavalin A affinity chromatography step by anion exchange chromatography; and separating the product of an anion exchange chromatography step by Heparin affinity chromatography so that a CEL I or CEL II protein is isolated. In a preferred embodiment, the method includes one or more Heparin affinity chromatography steps following the first heparin affinity chromatography step.

A further aspect of the present invention is a method for separating CEL I and CEL II in a mixture. The method involves subjecting a mixture containing CEL I and CEL II to heparin affinity chromatography so that CEL I and CEL II are separated.

A still further aspect of the present invention is a composition containing an isolated CEL II endonuclease. Preferably, the composition contains a CEL II endonuclease at a specific activity greater than 10,000,000 Units per mg protein as determined in a DNase solubilization assay at pH 8.5.

A further aspect of the invention is a method for detecting the presence of mismatches in double-stranded DNA using CEL II. The method involves contacting a sample containing double-stranded DNA with an isolated CEL II endonuclease, separating the product of the CEL II endonuclease digestion, and detecting said product. An increase in the number of double-stranded DNA fragments generated in the presence of the CEL II endonuclease is indicative of a mismatch in said DNA.

Another aspect of the invention is a kit for detecting the presence of mismatches in double-stranded DNA. The kit contains an isolated CEL II endonuclease enzyme and a DNA control.

BRIEF DESCRIPTION OF THE DRAWINGS

FIG. 6 shows a comparison of CEL I and CEL II mismatch cutting efficiency. A 632-bp heteroduplex DNA (400 ng) molecule containing a C/C and a G/G mismatch was digested in a 40 µl reaction mixture with 10 units (determined at pH 8.5) of CEL II (Profile A) and either 20 units (determined at pH 5.5) (Profile B) or 40 units (determined at pH 5.5) (Profile C) of CEL I for 20 minutes at 42° C. Reactions were stopped by the addition of 4 µL of 0.5 M EDTA. Digestion products (40 µL) were analyzed on the WAVE® HPLC system. Nuclease digestion products are 415 bp and 217 bp. The marker (M) shows peaks from left to right at 100, 200, 300, 400, 500, and 600 bp.

DETAILED DESCRIPTION OF THE INVENTION

Figure 1A:
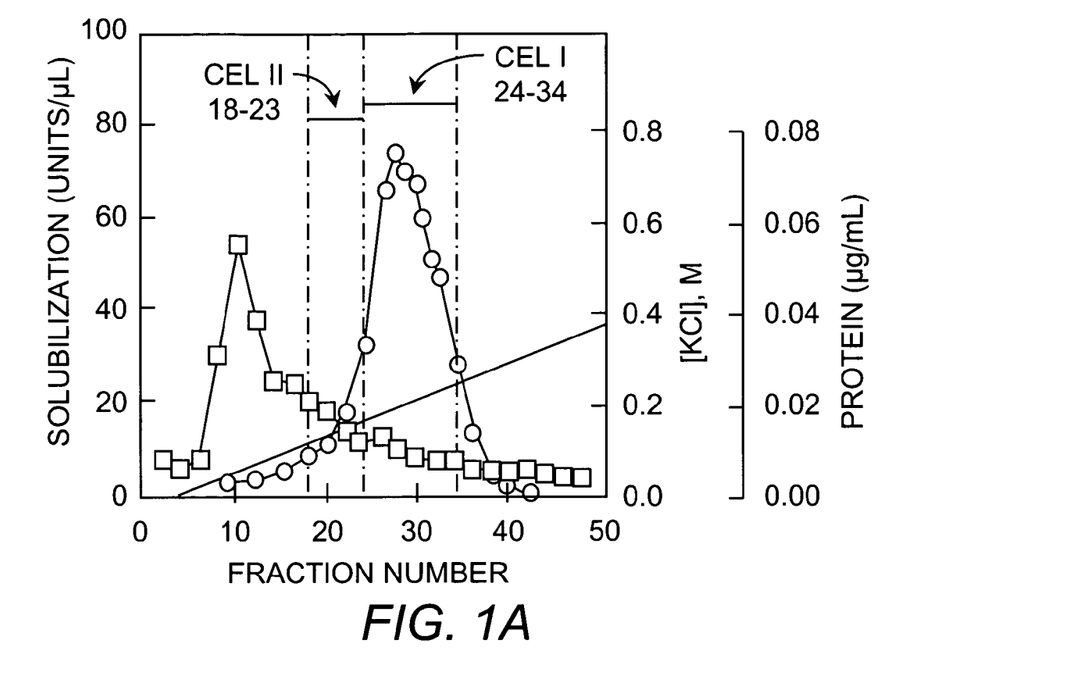
FIG. 1A shows a profile of nuclease activity and protein concentration in fractions eluted from a first heparin SEPHAROSE® column used in the purification of CEL I from CEL II. DNA solubilization activity (pH 5.5) (circles), protein concentration (squares) and KCl concentration (solid line) are shown for selected fractions.
Figure 1B:
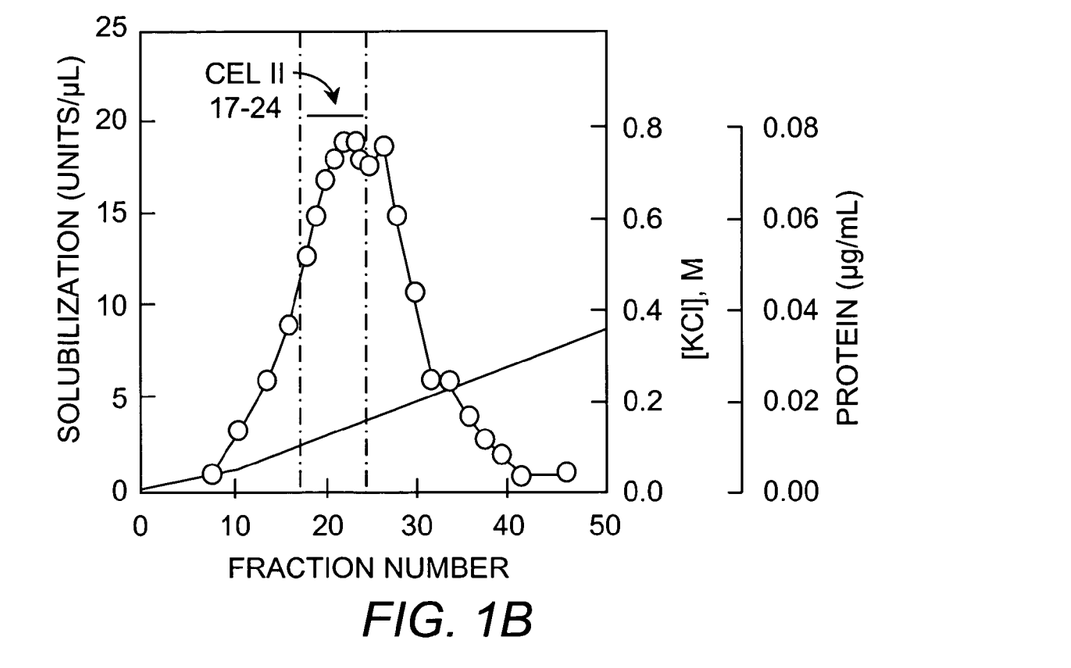
FIG. 1B shows a profile of nuclease activity and protein concentration in fractions eluted from a second heparin SEPHAROSE® column used in the purification of CEL II. Fractions 18 to 23 containing CEL II were pooled from the separation conducted in FIG. 1A, dialyzed to reduce KCl concentration, and separated by the second heparin SEPHAROSE® column. DNA solubilization activity (pH 5.5) (circles) and KCl concentration (solid line) are shown for selected fractions.

An improved method of isolating CEL I and CEL II has now been found. This method is a modification of established methods for preparing CEL I/CEL II nuclease mixtures (Yang, et al. (2000) supra). Specifically, a heparin SEPHAROSE® affinity chromatography step is added to the established method such that CEL I is substantially isolated from CEL II (FIG. 1A and FIG. 1B).

Using the final purification method of the invention, isolated preparations of CEL I had an average specific activity of $9.6 \times 10^7$ Units/mg (Table 1). Previously described preparations of CEL I nuclease, which contain both CEL I and CEL II, have a specific activity of $3.1 \times 10^7$ Units/mg (Yang, et al. (2000) supra).

TABLE 1

| | Solubilization Specific Activity[d] | | | |
|---|---|---|---|---|
| | pH 5.5 | | pH 8.5 | |
| Enzyme | Units/mg | fmole/Unit | Units/mg | fmole/Unit |
| CEL I[a] | $9.6 \times 10^7$ | 0.34 | $4.8 \times 10^7$ | 0.67 |
| CEL I[b] | $9.6 \times 10^7$ | 0.34 | $5.5 \times 10^7$ | 0.59 |
| CEL II[a] | $0.23 \times 10^7$ | 13.1 | $1.0 \times 10^7$ | 3.9 |
| CEL II[c] | $0.74 \times 10^7$ | 4.08 | $9.7 \times 10^7$ | 0.31 |

Figure 3:
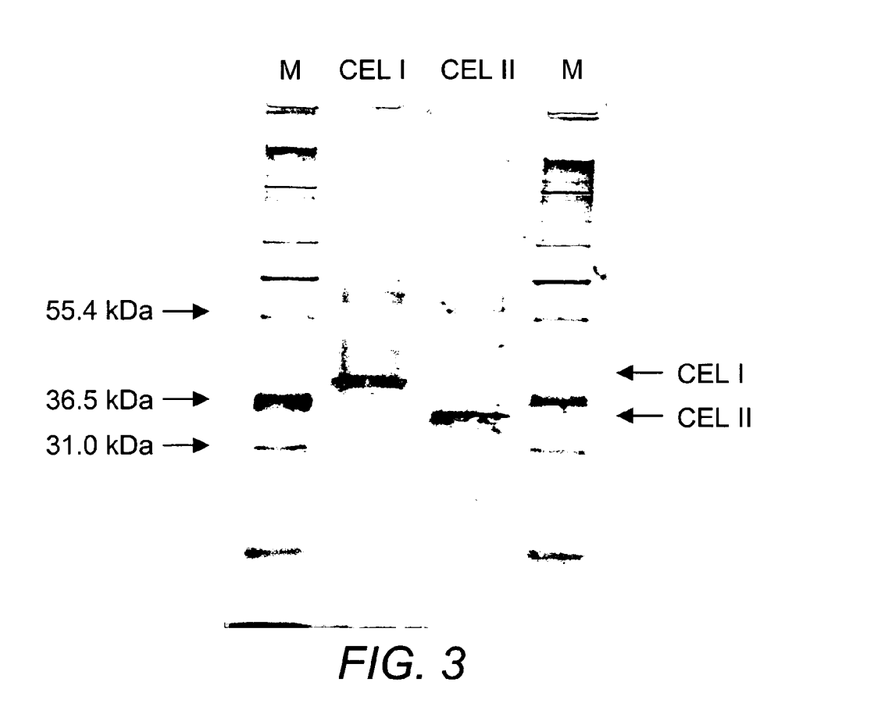
FIG. 3 is a photograph of a silver-stained 12% SDS-PAGE gel showing a Mono Q-concentrated fraction (0.4 µg) of CEL I and a Mono Q-concentrated fraction (0.5 µg) of CEL II from the preliminary purification procedure. Protein markers were run in lanes marked M.

[a]Specific activities were taken from the values for the MonoQ Concentrates in Table 3 (Preliminary Procedure) and were adjusted, assuming CEL I and CEL II were each 50% homogeneous based upon visual inspection of FIG. 3.
[b]Specific activities are the averages of the values for the MonoQ Concentrates from 4 different purifications performed according to Table 4 (Final Procedure) and adjusted for CEL I homogeneity based upon SDS-PAGE analysis.
[c]Specific activities are the averages of the values for the MonoQ Concentrates from 5 different purifications performed according to Table 4 (Final Procedure) and adjusted for CEL II homogeneity based upon SDS-PAGE analysis.
[d]One unit is the amount of enzyme required to produce 1 ng of acid-soluble material in 1 minute at 37° C.

Figure 2:
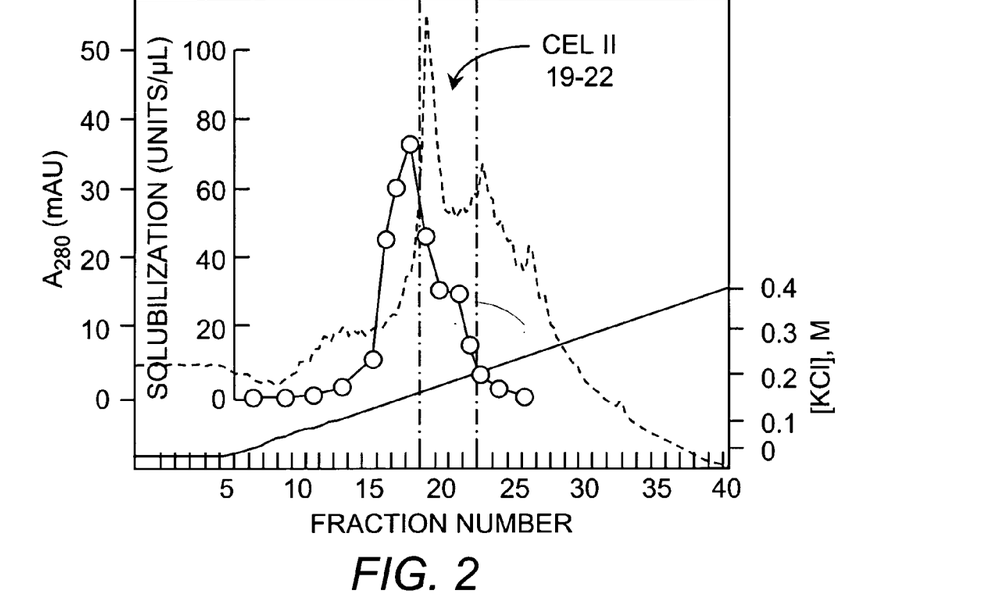
FIG. 2 shows a chromatographic profile of CEL II fractions eluted from a Mono Q column. Material loaded onto the Mono Q column was the peak CEL II fractions from the heparin SEPHAROSE® column shown in FIG. 1B. DNA solubilization activity (pH 5.5) (circles), protein concentration (dashed line) and KCl concentration (solid line) are shown for selected fractions.

After the initial heparin SEPHAROSE® column chromatography step, CEL II was further purified on a second heparin SEPHAROSE® column (FIG. 1B) and a Mono Q HR 5/5 column (FIG. 2).

SDS-PAGE analysis of the resulting purified CEL I and CEL II preparations isolated in preliminary experiments indicated single major protein bands corresponding to CEL I and CEL II, respectively (FIG. 3). CEL I migrated at an apparent molecular weight of 39 kDa and CEL II at 35 kDa. These sizes are near the previously reported molecular weights for CEL I and CEL II of 43 kDa and 39 kDa, respectively. A protein band corresponding to the expected molecular weight of CEL II was not detected in the CEL I preparation. CEL II was of similar purity to CEL I (~50–60% homogeneous) and contained a small amount of protein band corresponding to the apparent size of CEL I. As shown in FIG. 3, CEL I and CEL II preparations contained many of the same contaminants. Adjusting for contaminants, the specific activity of CEL I purified using the preliminary procedure was $9.6 \times 10^7$ and $4.8 \times 10^7$ units/mg at pH 5.5 and 8.5, respectively (Table 1). Adjusting for contaminants, the specific activity of CEL II purified using the preliminary procedure was $0.23 \times 10^7$ and $1.0 \times 10^7$ units/mg at pH 5.5 and 8.5, respectively (Table 1).

Using CEL I and CEL II enzymes purified in preliminary experiments, the pH optima of the enzymes were determined in a DNase solubilization assay. Table 2 shows that CEL I has optimal activity at pH 5.5 and CEL II has optimal activity at pH 8.5 or 9.0. By carrying out cross-column and pool assays at pH 5.5 and 8.5, the activities of each enzyme were monitored almost independently and enabled the rapid separation of CEL I and CEL II.

TABLE 2

| | DNA Solubilization Activity (Units) | | Relative Activity Setting Value at pH 5.5 at One | |
|---|---|---|---|---|
| pH | CEL I | CEL II | CEL I | CEL II |
| 5.0 | 43 | 45 | 0.9 | 0.6 |
| 5.5 | 48 | 71 | 1.0 | 1.0 |
| 6.25 | 49 | 83 | 1.0 | 1.2 |
| 6.75 | 42 | 98 | 0.9 | 1.4 |
| 7.0 | 37 | 133 | 0.8 | 1.9 |
| 7.5 | 31 | 203 | 0.65 | 2.9 |
| 8.0 | 26 | 302 | 0.55 | 4.2 |
| 8.5 | 25 | 321 | 0.5 | 4.5 |
| 9.0 | 23 | 324 | 0.5 | 4.6 |

To conduct a final purification of CEL I and CEL II and to prepare CEL II for amino acid sequence determination, the initial steps in the preliminary purification scheme were repeated through the ConA SEPHAROSE® column. Desalting of the ConA pool by G-25 SEPHADEX® column chromatography was used instead of dialysis to reduce the time required for desalting from 16 to 2 hours. The first Heparin SEPHAROSE® column was repeated with a shallower gradient to improve the separation of CEL I and CEL II. It was found that storage of CEL I or CEL II in phosphate-based buffers (i.e., Buffer B), even at −20° C., resulted in rapid loss of activity. After Heparin SEPHAROSE® chromatography, CEL I and II were partially separated and subsequent purification was pursued separately. To stabilize enzyme preparations for purification at a later time, the preparations were dialyzed against a Tris-HCl-based buffer (i.e., Buffer A). Both enzymes were stable stored at 4° C. in Buffer A.

Figure 4:
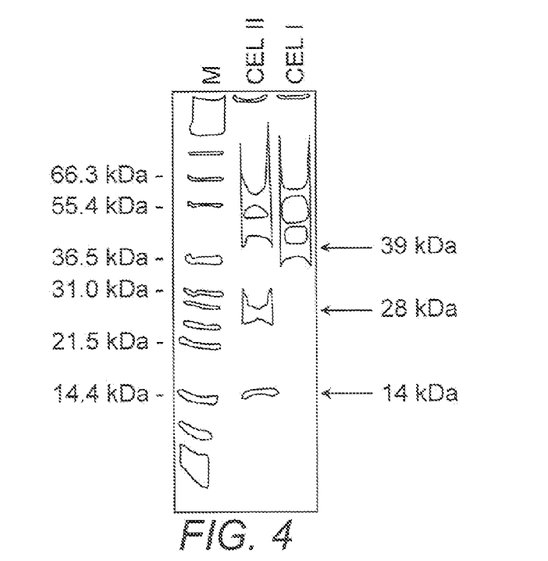
FIG. 4 is a photograph of a silver-stained 14% SDS-PAGE gel showing a final Mono Q-concentrated fraction (0.4 µg) of CEL I and a Mono Q-concentrated fraction (0.4 µg) of CEL II from the final purification procedure. Protein markers were run in lanes marked M.

CEL II was further purified by sequential chromatography on Mono S and Mono Q columns. An acidic pH was required for binding to Mono S. CEL II purified by this procedure was free of apparent contamination by CEL I, but was contaminated with two proteins that migrate as broad bands at 45 and 57 KDa (FIG. 4). These two glycosylated proteins were very difficult to separate from CEL II (and CEL I) without a severe loss in enzyme activity. After taking this contamination into consideration, the average specific activities of the CEL II purified by the final purification procedure were $9.7 \times 10^7$ and $0.74 \times 10^7$ units/mg at pH 8.5 and 5.5, respectively (Table 1). This was 3- to 10-fold higher than the specific activity of CEL II purified during the preliminary procedure (see Table 1). This difference may be attributed to delayed purification of CEL II during the preliminary procedure; CEL II preparations were stored for several weeks in phosphate buffer prior to separation by the second Heparin SEPHAROSE® column (FIG. 1B; Table 3), resulting in substantial loss of activity. Therefore, the specific activity assigned to CEL II purified by the final procedure more accurately reflects the true enzymatic activity of the enzyme.

FIG. 4 shows that, under reducing conditions (i.e., β-mercaptoethanol), CEL II migrates as two bands at 14 and 28 kDa in SDS-PAGE. Separation of CEL II under non-reducing conditions resulted in a single band of approximately 39 kDa. The two bands at 14 and 28 kDa are attributed to proteolytic cleavage of CEL II during purification. Most CEL II purified by the final purification procedure was proteolytically cut, however, occasionally some CEL II was obtained intact (FIG. 3). The cleavage of CEL II did not affect the functional mismatch cutting activity of the enzyme.

CEL I was further purified by HITRAPT™ Heparin SEPHAROSE® chromatography at acid pH and finally by passage over a Mono Q column. CEL I binds tighter to Heparin SEPHAROSE® at acid pH which shifts the enzyme away from most contaminants. CEL I purified by this procedure was free of apparent contamination by CEL II, but was contaminated with the same two proteins present in CEL II, although to a lesser degree (FIG. 4). After taking this contamination into consideration, the specific activity of the purified CEL I was $9.6 \times 10^7$ and $6.2 \times 10^7$ units/mg at pH 5.5 and 8.5, respectively (Table 4). These values are very similar to those determined for CEL I purified by the preliminary procedure (Table 3).

CEL I purified by either the preliminary purification procedure (FIG. 3) or the final purification procedure (FIG. 4) migrated at an apparent molecular weight of ~39 KDa on SDS-PAGE. CEL I was not proteolytically cleaved during purification.

Isolation of CEL I from CEL II facilitated the enzymatic characterization of these enzymes. There are a number of well-known methods used to assay the enzymatic activity of CEL nucleases (Oleykowski, et al. (1998) supra; Yang, et al. (2000) supra). Single-stranded DNA degradation activity of nucleases may be measured under acidic conditions or alkaline conditions, supercoiled DNA nicking activity may be monitored at a neutral pH, and the ability to cleave double-stranded DNA at mismatches may be determined at neutral pH in the presence of $Mg^{+2}$. In the purification scheme provided herein, the enzymatic specific activity of CEL I and CEL II was determined using single-stranded DNA as a substrate. At pH 8.5, CEL I and CEL II had similar activity (Table 1). However, at pH 5.5, CEL I was 13-times more efficient than CEL II in degrading single-stranded DNA (Table 1).

Figure 5:
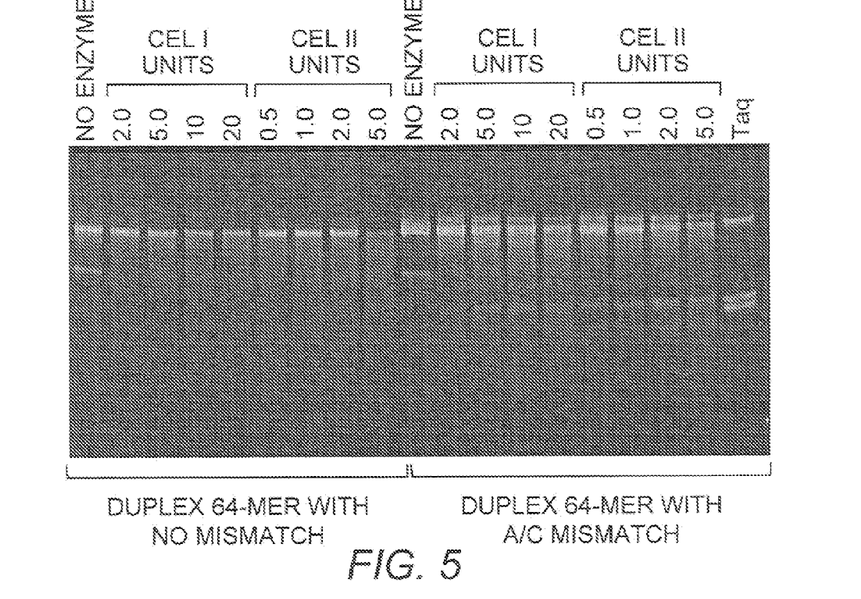
FIG. 5 is a photograph of a 12% non-denaturing gel showing digestion products derived from 500 ng of a duplex DNA oligonucleotide (64-mer) cut with various amounts of CEL I and CEL II. The duplex DNA oligonucleotide contained an A/C mismatch 35 nucleotides from the 5' end of upper strand. As a control, the A/C mismatch duplex DNA oligonucleotide was cut with Taq restriction endonuclease to generate duplex products of 32 and 30 base pairs with a two base pair overhang.

In an assay measuring the efficiency of cutting at an A/C mismatch, CEL II was found to be more efficient than CEL I (FIG. 5). Approximately 20 units (as determined at pH 5.5) of CEL I (7 fmoles) and 5 units (as determined at pH 8.5) of CEL II (1.7 fmoles) were required to cut a 64 nucleotide duplex DNA molecule to near completion at an A/C mismatch under conditions described herein (FIG. 5). CEL I has a higher amount of non-specific activity as evidenced by the appearance of more background digestion products generated by CEL I compared to CEL II and more loss of the smaller digestion product (compare lanes 14 and 18 of FIG. 5).

Figure 6:
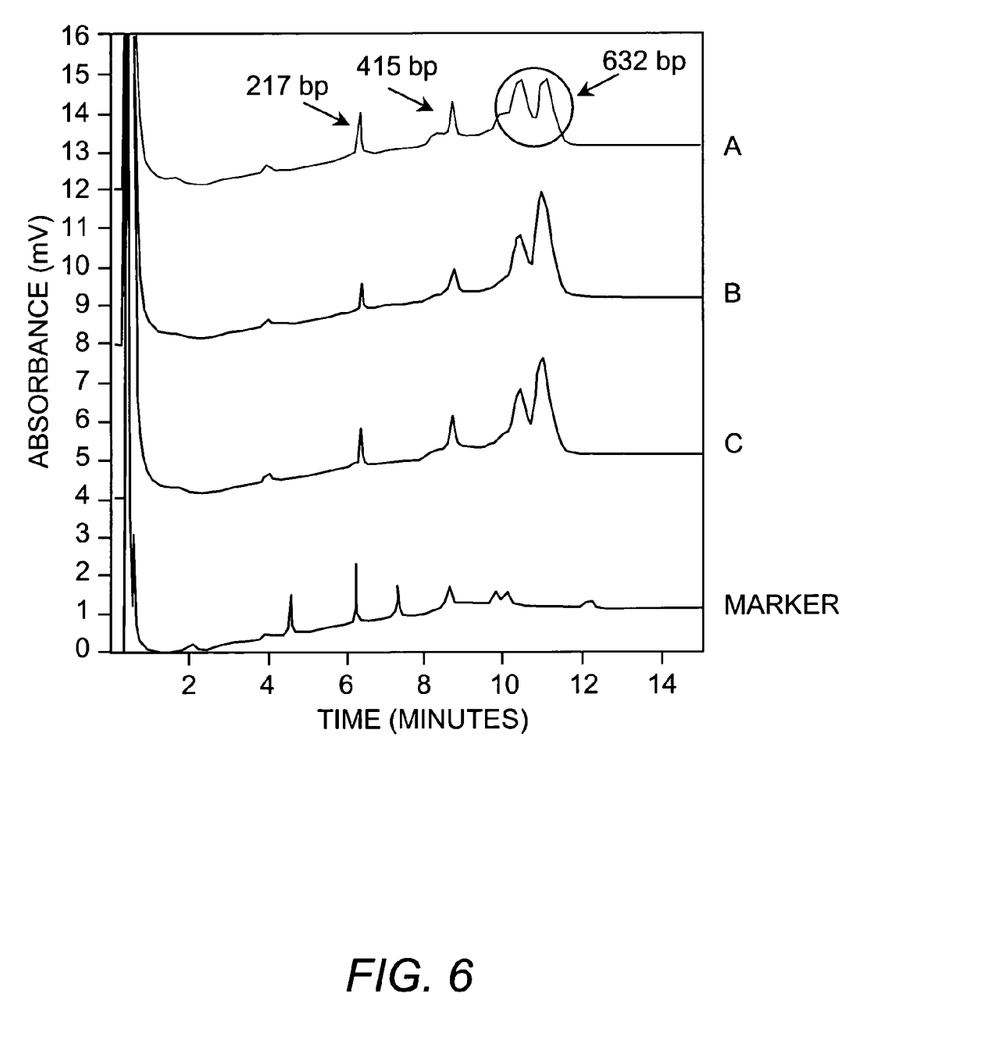

In a second assay which measures the efficiency of cutting a 50% heteroduplex/50% homoduplex mixture, wherein the heteroduplex is 50% G/G and 50% C/C, CEL II was again more efficient at cutting the mismatch (FIG. 6). Approximately 40 units (as determined at pH 5.5) of CEL I (14 fmoles) and 10 units (as determined at pH 8.5) of CEL II (3.4 fmoles) were required to cut the heteroduplex to the same extent.

As the preparations of CEL I and CEL II were not completely homogeneous, there is the possibility that some of the single-stranded DNase activity and nicking activity in CEL I and CEL II preparations tested was due to a contaminant. Thus, absolute specific activities for each enzyme may change upon further purification, e.g., the specific activity of CEL I in mismatch cutting assays will increase. However, as both CEL I and CEL II preparations appeared to have the same contaminants present, it is believed that the differences in specific activities of the two enzymes, as determined by the DNase solubilization and nicking assays, are principally due to the inherent properties of CEL I and CEL II endonucleases.

To further characterize the functional properties of CEL I and CEL II, the cutting efficiency of each enzyme was measured using various mismatched duplex DNA oligonucleotides (64-mers). The preferences of CEL I and CEL II were similar; C/C~C/T~A/C>T/T>A/A~G/G>>G/T~A/G. Accordingly, CEL I and CEL II appear to be related enzymes based upon their substrate specificity.

The amino terminal amino acid sequence of both the 18 kDa and 28 kDa fragment of CEL II were determined. The resulting sequences were:

14 KDa fragment: Xaa-Xaa-Lys-Gln-(Gly)-(His)-Phe-Ala-Ile-Xaa-Lys-Ile-Xaa-Gln-Xaa-(Phe) (SEQ ID NO:1), and 28 KDa fragment: Xaa-(Asn)-Asn-Xaa-Thr-Glu-Ala-Leu-Met (SEQ ID NO:2), where Xaa indicates the presence of an undefined amino acid residue and an amino acid in parenthesis indicates some uncertainty.

Based upon amino acid sequence homology with the CEL I protein, the 14 kDa fragment is derived from the amino terminal end of the CEL II protein and the 28 kDa fragment is derived from the carboxy end of the protein. Isolation of the gene encoding CEL II will be conducted by generating degenerate oligonucleotides based on the amino terminal sequence of both the 18 kDa and 28 kDa fragments. PCR amplicons generated therefrom will be cloned and sequenced, and the deduced amino acid sequence will be compared to the amino terminal sequences of the 18 kDa and 28 kDa fragments and the amino acid sequence of CEL I.

The results provided herein pertain to the isolation and characterization CEL I and CEL II. CEL I is much more efficient than CEL II in degrading single-stranded DNA (13-fold) at acid pH, but the two enzymes have similar solubilization activity at pH 8.5. In contrast, the efficiency of CEL II in cleaving DNA at mismatches is greater than that of CEL I. In addition, CEL I produces more non-specific degradation of matched duplex DNA than CEL II. Thus, isolated CEL II enzyme is desirable for use in applications requiring cleavage of DNA specifically at sites of base-substitution mismatch and DNA distortion without degrading matched duplex DNA.

Accordingly, one aspect of the present invention is a method for preparing an isolated CEL II or CEL I endonuclease protein. This aspect of the invention is based, in part, on the unexpected finding that when a mixture containing both CEL I and CEL II is applied to a Heparin SEPHAROSE® column, in particular a Heparin SEPHAROSE® Fast Flow column, that CEL I can be substantially isolated from CEL II. The resulting preparation of CEL II is substantially free of CEL I. Likewise, the preparation of CEL I endonuclease is substantially free of CEL II.

As used herein, CEL I and CEL II endonucleases are intended to include endonuclease enzymes of similar activity, pH optima, and size isolated from other non-recombinant or natural sources besides celery.

A method for preparing an isolated CEL II or CEL I endonuclease protein involves the steps of:
 a) extracting protein from a sample,
 b) separating the proteins by Concanavalin A affinity chromatography,
 c) separating the product of step b) by anion exchange chromatography, and
 d) separating the product of step c) by Heparin affinity chromatography.

In a preferred embodiment, the method further includes one or more additional Heparin affinity chromatographic separation steps.

In another preferred embodiment, the method further includes a step (e) of separating a product of step (d) by anion exchange chromatography. More preferably, the method includes a step (e) of separating the product of step (d) by anion exchange chromatography and step (f) of separating the product of step (e) by Heparin affinity chromatography.

A sample is intended to include any source containing a detectable amount of CEL I or CEL II endonuclease. A CEL I or CEL II endonuclease may be detected using any one of the suitable assays provided herein, an antibody which specifically recognizes CEL I and/or CEL II, or nucleic acid sequences which hybridize to sequences (e.g., DNA or RNA) encoding CEL I or CEL II endonuclease. Preferably, a sample is of a natural or non-recombinant source. A natural source may be of plant, microbial, or animal origin, preferably plant origin. When isolated from a plant source, the plant may be, for example, an alfalfa, asparagus, celery or tomato. Further, any tissue or organ may be used including, but not limited to, root, stem, leaf, flower or fruit.

In general, a protein extract is obtained by homogenizing or grinding a fresh or frozen sample, preferably fresh, in the presence or absence of a buffer. The particulate matter of the sample is then removed by subjecting the ground sample to centrifugation or filtration (e.g., through WHATMAN paper, cheesecloth, and the like). If the sample was not prepared in a buffer, it may be buffered following the centrifugation or filtration step. Buffers which may be used in accordance with the method of the invention include, but are not limited to, Tris, phosphate, tricine, HEPES, MOPS, and the like preferably containing proteases inhibitors such as phenylmethyl sulfonyl fluoride (PMSF), aprotinin, chymostatin, antipain, peptstatin A or combinations thereof to inhibit protein degradation. A buffer may further contain salts, detergents, or organic chemicals to enhance the extraction or stabilization of proteins of the sample, however, such components should not interfere with the chromatographic separation steps of the invention.

As used herein, columns which may be suitable for use in the anion exchange chromatography step of the invention include, but are not limited to, a Mono Q column, Diethylaminoethane (DEAE) column, and the like. Preferably, a Mono Q resin is used in a method of isolating CEL II or CEL I.

In the chromatographic separation steps of the invention, the Concanavalin A, anion exchange, and Heparin may be attached to a wide variety of supports or resins such as cellulose, agarose, porous beads or SEPHAROSE®. Preferably, the Heparin and Concanavalin A affinity columns have a SEPHAROSE®-based support. A preferred anion exchange column for use in the method of the invention is Mono Q 5/5 HR.

The products of the various purification steps may be analyzed for CEL endonuclease activity using one or more well-known assays including, but not limited to, a DNA nicking assay, a DNase solubilization assay, or a mismatch endonuclease assay. The products of the various purification steps may also be analyzed by electrophoretic separation, such as polyacrylamide gel electrophoresis.

Another aspect of the present invention is an isolated CEL I or CEL II endonuclease protein from a sample separated by at least one, and preferably two or more Heparin affinity column chromatography purification steps. A CEL I endonuclease preparation is said to be substantially free of a CEL II endonuclease if the ratio of single-stranded DNA solubilization activity determined at pH 8.5 versus pH 5.5 is <0.2, <0.4, <0.6, preferably <0.8. Likewise, a CEL II endonuclease preparation is said to be substantially free of a CEL I endonuclease if the ratio of single-stranded DNA solubilization activity determined at pH 8.5 versus pH 5.5 is >25, >20, >15, preferably >10.

The presence of CEL I may be determined by the presence of a single major protein band of approximately 39 kDa on a reducing or non-reducing gel without removal of N-linked oligosaccharides. The presence of CEL II may be determined by the presence of a single major protein band (at approximately 35 kDa) or two major protein bands (approximately 14 and 28 kDa) under non-reducing or reducing gel conditions, respectively, without removal of N-linked oligosaccharides. Furthermore, CEL I and CEL II endonucleases may be distinguished by their pH optima in a DNase solubilization assay; CEL I has optimal activity at pH 5.5 and CEL II has optimal activity at pH 8.5 or 9.0.

Another aspect of the invention provides a method for separating CEL I and CEL II in a mixture by subjecting said mixture to Heparin affinity chromatography. A mixture may be a product of a chromatography step or may be protein extract from a sample.

A further aspect of the present invention is a composition comprising CEL II, said composition being substantially free from CEL I. In one embodiment, the CEL II in said composition is present in said composition with a specific activity of >200,000,000; >150,000,000; >100,000,000; >50,000,000; >25,000,000; preferably >10,000,000 units/mg protein as determined by DNA solubilization at pH 8.5. DNA solubilization may be determined in a DNase solubilization assay in which the substrate is, for example, denatured calf thymus.

A further aspect of the present invention is a method for detecting the presence of mismatches in double-stranded DNA or determining the site of a mutation in double-stranded DNA using an isolated CEL II endonuclease of the invention. Examples of such methods are found in U.S. Pat. Nos. 5,869,245 and 6,027,898. It is contemplated that this method may be used for analyzing a sample of double-stranded DNA to determine the presence of a mutation therein. The method involves contacting a sample (e.g., a biological sample, cells, tissue, etc.) containing double-stranded DNA with an isolated CEL II endonuclease, separating the product of the CEL II endonuclease digestion, and detecting said product. An increase in the number of fragments (i.e., CEL II digestion of one band into two or more bands as determined on an agarose gel) or decrease in the size of the double-stranded DNA in the presence of the CEL II endonuclease is indicative of a mismatch in said DNA. The step of separating the product of the CEL II endonuclease digestion may be carried out using gel electrophoresis, capillary electrophoresis, or chromatographic separation such as Matched Ion Polynucleotide Chromatography, size exclusion chromatography, ion exchange chromatography, or reverse phase chromatography. Standard methods of detecting a double-stranded DNA molecule are well-known in the art (e.g., ethidium bromide staining or UV absorbance).

In another aspect, the invention provides a kit for detecting the presence of mismatches in double-stranded DNA or determining the site of a mutation in double-stranded DNA. A kit of the invention includes a composition containing an isolated CEL II endonuclease.

A composition containing an isolated CEL II endonuclease is intended to include a CEL II endonuclease, wherein said CEL II has been prepared using a purification procedure that includes at least one Heparin affinity chromatography step; a CEL II endonuclease, wherein said CEL II is substantially free of CEL I; or a CEL II endonuclease having a specific activity >200,000,000; >150,000,000; >100,000,000; >50,000,000; >25,000,000; preferably greater than 10,000,000 units/mg protein as determined by DNA solubilization at pH 8.5.

A kit of the invention may also contain a control DNA component for detecting CEL II endonuclease activity. A control DNA component may be, for example, a double-stranded DNA that includes a site of mismatch (e.g., a duplex oligonucleotide of 64-bp in length as described herein) or a standard DNA mixture comprising double-stranded DNA fragments, wherein said mixture comprises double-stranded DNA that includes a site of mismatch when said mixture is subjected to a hybridization procedure (e.g., a mixture of a 209-base pair DNA mutation standard as supplied by Transgenomic, Omaha, Nebr.).

A kit may further contain one or more buffers or reagents for use in a reaction that includes CEL II endonuclease. Suitable buffers or reagents include, for example, a buffer that yields the following concentrations in such a reaction: 20 mM Tris-HCl (pH 7.4), 25 mM KCl, 10 mM $MgCl_2$; Taq DNA polymerase; or a stopping solution comprising 0.5 M EDTA.

The invention is described in greater detail by the following non-limiting examples.

EXAMPLE 1

Materials and Assays

Plasmid DNA pUC19 was isolated using well-established methods (Sambrook, et al. (1989) *Molecular Cloning: A Laboratory Manual,* 2nd Ed., Cold Spring Harbor Laboratory, Cold Spring Harbor, N.Y.). Calf thymus DNA (SIGMA, St. Louis, Mo.) was purified by repeated cycles of proteinase K treatment and phenol extraction, reduced in viscosity by sonication, and denatured by heating in a boiling water bath for 10 minutes followed by quick cooling on ice. Q SEPHAROSE® Fast Flow, Heparin SEPHAROSE® Fast Flow, G-25 SEPHADEX®, Con A-SEPHAROSE® matrices, HIPREP™ 16/10 Heparin SEPHAROSE® Fast Flow, Mono S HR 5/5, HITRAP™ Heparin HP, and Mono Q HR 5/5 columns were purchased from Amersham Pharmacia Biotech (Piscataway, N.J.). Phosphocellulose P-11 from WHATMAN® (Ann Arbor, Mich.). Synthetic oligonucleotides were from (INVITROGEN™, Carlsbad, Calif.).

Mismatch Cutting Assay with PCR Fragments. Plasmid pQIS155 contains a derivative of the gene for CEL I (Yang et al. (2000) supra) cloned between the XhoI and NdeI sites of pET22b (NOVAGEN®, Madison, Wis.). Using a GENETAILOR™ Site-Directed Mutagenesis System (INVITROGEN™), a C to G substitution was generated at position 605 of the CEL I gene of pQIS155 thereby creating the target site. Plasmid DNAs were transformed into *E. coli* DH5α (INVITROGEN™) and cells were grown in LB medium+ 100 μg/mL ampicillin. Plasmid DNA was isolated using a Plasmid Mini Kit (QIAGEN®, Valencia, Calif.). Plasmids were named based upon their sequence at the target site, e.g., pQIS155G has a G at the target site.

A 632-bp fragment was amplified from pQIS155 and pQIS155G plasmid DNA utilizing the following primers: pCELR: 5'-CGC CAA AGA ATG ATC TGC GGA GCT T (SEQ ID NO:3) and pCEL190F: 5'-ACA CCT GAT CAA GCC TGT TCA TTT GAT TAC (SEQ ID NO:4). PCR was performed with OPTIMASE® Polymerase (Transgenomic, Omaha, Nebr.) utilizing the recommended reaction conditions. The amount and quality of the amplified DNA produced in a PCR reaction were determined by visual comparison of the DNA product to a DNA mass ladder (NEB, Beverly, Mass.) fractionated by agarose gel electrophoresis. Heteroduplexes were formed by annealing equal amounts of amplified DNA prepared from pQIS155 and pQIS155G. DNA hybridization was performed in a thermocycler using the following program: 95° C. for 10 minutes; 95° C. to 85° C. at −2° C./second; and 85° C. to 25° C. at −0.1° C./second. When two different alleles are annealed in a 1:1 mixture mismatch heteroduplexes are formed approximately 50% of the time. For each base change, two mismatches are formed. Reformed homoduplexes constitute the other 50% of the population.

Annealed DNA (400 ng) was digested using the desired amount of CEL I or CEL II in a 40-μl volume containing 20 mM Tris-HCl, pH 7.4, 25 mM KCl, and 10 mM $MgCl_2$. The digestion reaction was incubated at 42° C. for 20 minutes and was stopped by addition of 4 μl of 0.5 M EDTA.

Cleavage products (40 μl) generated with CEL I or CEL II were separated on a WAVE® system using UV detection at 260 nm (Transgenomic). A DNASEP® Cartridge was run at 50° C. under non-denaturing conditions to separate DNA fragments based upon size.

Nicking Assay. Reaction mixtures (20 μL) containing 20 mM HEPES (pH 7.5), 10 mM NaCl, 3 mM $MgCl_2$, 500 ng RF-I pUC19, and various amounts of CEL nuclease were incubated at 37° C. for 15 minutes. Enzyme activity was terminated by the addition of 5 μL of 35% (w/v) sucrose, 25 mM EDTA, 0.5% (w/v) sodium dodecyl sulfate (SDS), and 0.2% (w/v) bromophenol blue. A 10 μL aliquote of the reaction mixture was loaded onto a 1% agarose gel, separated at 7 V/cm for 2 hours, stained with ethidium bromide, photographed using a KODAK EDAS 290 System and the RF-I band was quantified using the EDAS system software. One nicking unit is defined as the amount of enzyme required to convert 1 μg of pUC19 RF-I DNA to RF-II or RF-III DNA in 1 minute at 37° C.

DNase Solubilization Assay. Solubilization assays were carried out at pH 5.5 and 8.5. Reaction mixtures (50 μL) at pH 5.5 contained 20 mM sodium acetate (pH 5.5), 10 mM KCl, 0.5 mg/mL denatured calf thymus DNA, and various amounts of CEL nuclease. Reaction mixtures at pH 8.5 contained the same components except the buffer was 20 mM Tris-HCl (pH 8.5), 10 mM KCl and 3 mM $MgCl_2$. Reactions were incubated at 37° C. for 15 minutes and enzyme activity was terminated by the addition of 50 µL of cold 20 mM $LaCl_3$ in 0.2 N HCl. After centrifugation in an EPPENDORF microfuge at 13,000 rpm for 10 minutes, the absorbance of the supernatant at 260 nm was measured using a spectrophotometer to determine the amount of DNA solubilized. One unit of solubilization activity (a CEL Nuclease Unit) is the amount of enzyme required to produce 1 ng of acid-soluble material in 1 minute at 37° C.

Mismatch Endonuclease Assay with Oligonucleotides. Mismatch endonuclease assays were performed according to standard methods (Oleykowski, et al. (1998) supra) using blunt-end matched and mismatched DNA duplexes of 64 nucleotides in length. Where appropriate, DNA oligonucleotides were labeled at the 5' end with [$\gamma$-$^{32}$P] ATP and T4 polynucleotide kinase (Sambrook, et al. (1989) supra). Reaction mixtures (20 µL) contained 20 mM Tris-HCl (pH 7.4), 25 mM KCl, 10 mM $MgCl_2$, 500 ng unlabeled 64-mer duplex DNA or 5 ng 5'-end labeled duplex, and CEL nuclease. When labeled duplex was used, Taq DNA polymerase (2.5 Units; PROMEGA®, Madison, Wis.) was added to the reaction and incubated at 42° C. for 5 minutes. When 500 ng of duplex DNA was used, the incubation was at 42° C. for 30 minutes. Subsequently, Proteinase K (2 µg) was added and the reaction was incubated an additional 5 minutes at 42° C. Reactions were terminated by the addition of 1.5 µL of 70% (w/v) sucrose, 50 mM EDTA, 5 mM 1,10 phenanthroline, 0.1% (w/v) xylene cyanol, and 0.4% (w/v) bromophenol blue. DNA was fractionated on a 12% PAGE gel. Unlabeled DNA was separated on gels lacking urea and the gel was stained with ethidium bromide and photographed as described herein. Labeled DNA was separated on gels containing and lacking 7 M urea. The gels were subsequently dried and analyzed using a PHOSPHORIMAGER® (Molecular Dynamics, Sunnyvale, Calif.).

Protein Analysis. SDS-Polyacrylamide Gel Electrophoresis (SDS-PAGE) was carried out using standard methods (Sambrook, et al. (1989) supra) and 12% precast polyacrylamide gels (INVITROGEN™, Carlsbad, Calif.). Proteins bands were detected by silver stain (BIO-RAD®, Hercules, Calif.). MARK12™ protein standards (INVITROGEN™) were used to determine apparent molecular weights.

Protein concentrations were determined using a bicinchoninic acid protein assay (Pierce, Rockford, Ill.) with bovine serum albumin as a standard.

EXAMPLE 2

Preliminary Purification of CEL Nucleases

All purification steps were performed at 4° C. During column chromatography, nuclease activity was monitored with both the DNase solubilization assay at pH 5.5 and the RF-I nicking assay.

Preparation of Crude Extract. Chilled celery stalks (10 Kg; 10 bunches) were minced in a food processor and homogenized with a WARING® blender. The juice was collected from the pulp by squeezing the pulp to dryness through four layers of cheesecloth. The juice was centrifuged at 5000×g for 20 minutes to remove green particulate material. The clarified, amber-colored juice (7.7 Liters) was adjusted to the composition of ConA Buffer (100 mM Tris-HCl, pH 7.7, 100 µM phenylmethyl sulfonyl fluoride (PMSF)) by the addition of 1 M Tris-HCl, pH 7.7, and 0.1 M PMSF. Solid $(NH_4)_2SO_4$ was added to the juice to 80% saturation (51.6 g/100 mL) and the suspension was stirred overnight. The suspension was centrifuged at 10,000×g for 30 minutes to recover a protein pellet. The pellet was dissolved in 700 mL ConA Buffer. $(NH_4)_2SO_4$ was added to the resuspended pellet to 15% saturation (8.4 g/100 mL), stirred for 30 minutes, centrifuged at 10,000×g for 30 minutes, and the supernatant was kept for further analysis.

Concanavalin A-SEPHAROSE® Affinity Chromatography. Con A SEPHAROSE® (100 mL), cross-linked with dimethyl suberimidate, was packed into a 2.5-cm diameter column and equilibrated in ConA Wash Buffer (ConA Buffer containing 0.5 M KCl). The $(NH_4)_2SO_4$ supernatant was loaded onto the column at a flow rate of 0.75 mL/minute overnight. The column was disassembled and the resin was washed in a Buchner funnel with 6 to 8 Liters of ConA Wash Buffer. The washed resin was repacked into a 2.5-cm column using ConA Wash Buffer. CEL nucleases were eluted with 100 mL of ConA Wash Buffer containing 0.5 M $\alpha$-methyl-mannoside. The elution was repeated 6 times. Eluants were combined and TRITON™ X-100 was added to a final concentration of 0.01%. Subsequently, the eluted nuclease solution was dialyzed overnight against Buffer A (50 mM Tris-HCl, pH 8.0, 5 mM $\alpha$-methyl-mannoside, 0.01% TRITON™ X-100) containing 100 µM PMSF.

Q SEPHAROSE® Chromatography. The dialyzed eluant was loaded onto a 50 mL Q SEPHAROSE® Fast Flow column (2.5×10 cm) equilibrated with Buffer A containing 45 mM $\alpha$-methyl-mannoside. Subsequently, the column was washed with 250 mL of Buffer A containing 45 mM $\alpha$-methyl-mannoside and CEL nucleases were eluted with a 500-mL linear gradient of 0 to 0.5 M KCl in Buffer A containing 45 mM $\alpha$-methyl-mannoside. A large peak of DNA exonuclease activity, identified using the solubilization assay at pH 5.5 but not the nicking assay, eluted from Q SEPHAROSE® between 0.05 and 0.12 KCl. The CEL nucleases eluted between 0.12 and 0.22 KCl. CEL nuclease peak fractions were pooled and dialyzed against Buffer B (25 mM $KPO_4$, pH 7.0, 5 mM $\alpha$-methyl-mannoside, 0.01% TRITON™ X-100) containing 100 µM PMSF.

Heparin SEPHAROSE® Chromatography. Pooled and dialyzed CEL nuclease fractions were loaded onto a 20-mL heparin SEPHAROSE® Fast Flow column (0.6×18 cm) equilibrated in Buffer B containing 45 mM $\alpha$-methyl-mannoside. Subsequently, the column was washed with 100 mL of Buffer B containing 45 mM $\alpha$-methyl-mannoside and CEL nucleases were eluted with a 200-mL linear gradient of 0 to 0.4 M KCl in Buffer B containing 45 mM $\alpha$-methyl-mannoside. CEL I and CEL II were partially separated by heparin SEPHAROSE® chromatography. Because CEL I has a much higher specific activity than CEL II in the solubilization assay at pH 5.5 (Table 1), the cross-column activity profile established with this assay method was dominated by CEL I. Therefore, activity profiles did not reflect the presence of CEL II as a distinct peak or even a shoulder (FIG. 1A).

CEL II was pooled based upon identification of its presence by SDS-PAGE. CEL II eluted between 0.06 and 0.18 M KCl. CEL I eluted between 0.12 and 0.22 M KCl. Separate pools were made of fractions in these KCl concentration ranges and the CEL nuclease present in each pool was purified separately. CEL I was purified first. CEL II was stored frozen and thawed for further purification.

Phosphocellulose P-11 Chromatography of CEL I (Preliminary). The CEL I pool from the heparin SEPHAROSE® column was diluted 1:1 with Buffer B containing 45 mM $\alpha$-methyl-mannoside and loaded onto a 2.5-mL (0.9×4 cm) P-11 column equilibrated in Buffer B containing 45 mM $\alpha$-methyl-mannoside. The column was washed with 10 mL of Buffer B containing 45 mM α-methyl-mannoside and 0.1 M KCl. CEL I was eluted with a 25-mL linear gradient of 0.1 to 1.0 M KCl in Buffer B containing 45 mM α-methyl-mannoside. CEL I eluted between 0.2 and 0.6 M KCl. Peak fractions of CEL I were pooled and dialyzed against Buffer A.

Mono Q Chromatography of CEL I (Preliminary). The dialyzed pool of CEL I from the P-11 column was loaded onto a Mono Q HR 5/5 column equilibrated in Buffer A containing 45 mM α-methyl-mannoside. The column was washed with 5 mL of Buffer A containing 45 mM α-methyl-mannoside and CEL I was eluted with a 20-mL linear gradient of 0 to 0.4 M KCl in Buffer A containing 45 mM α-methyl-mannoside. CEL I eluted between 0.14 and 0.18 M KCl. Peak fractions of CEL I activity were pooled and dialyzed against Storage Buffer (50 mM Tris-HCl, pH 7.5, 100 mM KCl, 0.01% TRITON™ X-100, 10 μM ZnCl$_2$, and 50% (v/v) glycerol).

Repeat Heparin SEPHAROSE® Chromatography of CEL II (Preliminary). CEL II was pooled from the initial heparin SEPHAROSE® column and dialyzed against Buffer B. The dialyzed pool was loaded onto a 5-mL heparin SEPHAROSE® column (0.9×8 cm) equilibrated in Buffer B containing 45 mM α-methyl-mannoside. The column was washed with 25 mL Buffer B containing 45 mM α-methyl-mannoside and CEL II was eluted with a 50-mL linear gradient of 0 to 0.4 M KCl in Buffer B containing 45 mM α-methyl-mannoside. CEL II eluted between 0.09 and 0.15 M KCl (FIG. 1B). Peak fractions of CEL II activity were pooled and dialyzed against Buffer A.

Mono Q Chromatography of CEL II (Preliminary). Dialyzed CEL II eluted from the second heparin SEPHAROSE® column was loaded onto a Mono Q HR 5/5 column equilibrated in Buffer A containing 45 mM α-methyl-mannoside. The column was washed with 5 mL of Buffer A containing 45 mM α-methyl-mannoside and CEL II was eluted with a 20-mL linear gradient of 0 to 0.4 M KCl in Buffer A containing 45 mM α-methyl-mannoside. CEL II eluted between 0.18 and 0.21 M KCl (FIG. 2). Peak fractions of CEL II activity were pooled and dialyzed against Storage Buffer.

Preliminary Recovery of CEL I and CEL II. Table 3 provides the recovery of CEL I and CEL II nucleases purifed from celery by the preliminary purification procedure.

TABLE 3

| Fraction | Volume (mL) | Protein Conc. (mg/mL) | Total Protein (mg) | Unit Activity (Units/mL)[a] |
|---|---|---|---|---|
| Clarified Crude | 7673 | 6.8 | 52176 | 24,000 |
| (NH$_4$)$_2$SO$_4$ | 800 | 7.3 | 5840 | 50,000 |
| Con A SEPHAROSE ® | 600 | 0.47 | 284 | 23,000 |
| Q SEPHAROSE ® | 60 | 0.43 | 26 | 76,000 |
| Heparin SEPHAROSE ® CEL I | 43 | 0.01 | 0.43 | 56,000 |
| Phosphocellulose P-11 CEL I | 7.4 | 0.019 | 0.14 | 201,000 |
| Mono Q Concentrate CEL I[b] | 0.45 | 0.04 | 0.018 | 1,910,000 |
| Heparin SEPHAROSE ® CEL II | 38 | 0.015 | 0.57 | 7,000 |
| Heparin SEPHAROSE ® #2 CEL II | 10 | 0.012 | 0.12 | 15,000 |
| Mono Q Concentrate CEL II[c] | 0.43 | 0.1 | 0.043 | 110,000 |

| Fraction | Total Activity (Units)[a] | Specific Activity (Units)[a] | Fold Purification | % Recovery |
|---|---|---|---|---|
| Clarified Crude | 1.84 × 10$^8$ | 3,500 | 1 | 100 |
| (NH$_4$)$_2$SO$_4$ | 4.00 × 10$^7$ | 6,900 | 6.9 | 22 |
| Con A SEPHAROSE ® | 1.40 × 10$^7$ | 49,000 | 14 | 8 |
| Q SEPHAROSE ® | 4.60 × 10$^6$ | 177,000 | 50 | 2.5 |
| Heparin SEPHAROSE ® CEL I | 2.40 × 10$^6$ | 5,600,000 | 1,600 | 1.3 |
| Phosphocellulose P-11 CEL I | 1.50 × 10$^6$ | 10,710,000 | 3,060 | 0.8 |
| Mono Q Concentrate CEL I[b] | 8.60 × 10$^5$ | 47,800,000 | 13,660 | 0.5 |
| Heparin SEPHAROSE ® CEL II | 2.60 × 10$^5$ | 456,000 | 130 | 0.14 |
| Heparin SEPHAROSE ® #2 CEL II | 1.50 × 10$^5$ | 1,250,000 | 360 | 0.08 |
| Mono Q Concentrate | 4.95 × 10$^4$ | 1,150,000 | 330 | 0.03 |

TABLE 3-continued

CEL II[c]

[a]CEL Nuclease Units determined by the solubilization assay at pH 5.5.
[b]~50% CEL I with no discernible CEL II present as determined by FIG. 3.
[c]~50% CEL II with <10% CEL I present as determined by FIG. 3.

EXAMPLE 3

Final Purification of CEL Nucleases

All purification steps were performed at 4° C. During column chromatography, nuclease activity was monitored with both the DNase solubilization assay at pH 5.5 and 8.5.

Preparation of Crude Extract. Chilled celery stalks (15–20 bunches) were minced in a food processor and homogenized in a WARING® blender. The juice was collected from the pulp by squeezing the pulp to dryness through 4 layers of cheesecloth. The juice was centrifuged at 5,000×g for 20 minutes to remove green particulate material. The clarified amber-colored juice was adjusted to the composition of ConA Buffer (100 mM Tris-HCl, pH 7.7, 100 µM PMSF) by the addition of 1 M Tris-HCl (pH 7.7) and 0.1 M PMSF. Solid $(NH_4)_2SO_4$ was added to the juice to 80% of saturation (51.6 g/100 mL) and the suspension was stirred for 2 hours. The suspension was centrifuged at 10,000×g for 30 minutes to recover a protein pellet. The pellet was dissolved in 700–800 mL of ConA Buffer. $(NH_4)_2SO_4$ was dissolved to 15% of saturation (8.4 g/100 mL) and the suspension was stirred for 30 minutes. The suspension was centrifuged at 10,000×g for 30 minutes and the pellet was discarded.

Concanavalin A-SEPHAROSE® Affinity Chromatography. Con A-SEPHAROSE® (100 mL) (cross-linked with dimethyl suberimidate) was packed into a 2.5-cm diameter column and equilibrated in ConA Wash Buffer (ConA Buffer containing 0.5 M KCl). The $(NH_4)_2SO_4$ supernatant was loaded overnight onto the column at a flow rate of 0.75 mL/minute. The column was subsequently disassembled and the resin was washed in a Buchner funnel with 6–8 liters of ConA Wash Buffer. The washed resin was repacked into the 2.5-cm column using ConA Wash Buffer. CEL nucleases were eluted with 100 mL of ConA Wash Buffer containing 0.5 M α-methyl-mannoside. The elution was repeated 4 more times. Eluants were combined and TRITON™ X-100 was added to a final concentration of 0.01%.

G-25 SEPHADEX® Chromatography (Final). The ConA-SEPHAROSE® pool was desalted on a 2 L (10×26 cm) G-25 SEPHADEX® column equilibrated in Buffer A (50 mM Tris-HCl, pH 8.0, 5 mM α-methyl-mannoside, 0.01% TRITON™ X-100). The column was developed in Buffer A containing 100 µM PMSF at 25–30 mL/minute. Proteins were eluted in an elution volume between 700 and 1,400 mL. Eluants were pooled and 1 M α-methyl-mannoside was added to a final concentration of 50 mM α-methyl-mannoside.

Q SEPHAROSE® Chromatography (Final). The desalted ConA pool was loaded unto a 50-mL Q SEPHAROSE® Fast Flow column (2.5×10 cm) equilibrated overnight with Buffer A containing 45 mM α-methyl-mannoside at ~0.5 mL/minute. The column was washed with 250 mL of Buffer A containing 45 mM α-methyl-mannoside. CEL nucleases were eluted with a 500-mL linear gradient of 0 to 0.5 M KCl in Buffer A containing 45 mM α-methyl-mannoside. A large peak of DNA exonuclease activity, identified in the solubilization assay at pH 5.5 but not at pH 8.5, was sometimes observed eluting from Q SEPHAROSE® between 0.05 and 0.12 M KCl. CEL nucleases eluted between 0.12 and 0.18 M KCl based upon the solubilization assay at pH 5.5, and between 0.12 and 0.3 M KCl based upon the solubilization assay at pH 8.5. Fractions between 0.12 M and 0.25 M KCl were pooled, thereby avoiding the exonuclease at low concentrations of KCl and the major protein contaminants at high concentrations of KCl. Fractions above 0.25 M KCl was avoided as the bulk of contaminating proteins eluted as the KCl concentration increased. There was a compromise between pooling all of the CEL II activity (active at pH 8.5) and excluding the contaminating proteins that eluted at higher concentrations of KCl. The CEL I and CEL II were pooled together and dialyzed against Buffer B (25 mM $KPO_4$, pH 7.0, 5 mM α-methyl-mannoside, 0.01% TRITON™ X-100) containing 100 µM PMSF.

Heparin SEPHAROSE® Chromatography (Final). To the dialyzed CEL nuclease pool from Q SEPHAROSE® was added α-methyl-mannoside to a final concentration of 50 mM. The CEL nuclease pool was loaded onto a 20-mL HIPREP™ 16/10 Heparin FF column (0.6×18 cm) equilibrated in Buffer B containing 45 mM α-methyl-mannoside at 1 mL/minute. The column was washed with 100 mL of Buffer B containing 45 mM α-methyl-mannoside at 2 mL/minute. The CEL nucleases were eluted with a 200-mL linear gradient of 0 to 0.3 M KCl in Buffer B containing 45 mM α-methyl-mannoside and 100 µM PMSF at 2 mL/minute with 4 mL/fraction. Fractions were assayed at pH 5.5 and 8.5. CEL I and CEL II were partially separated by Heparin SEPHAROSE® chromatography. The major peak of protein contaminants eluted at 0.02 to 0.12 M KCl. CEL II (more active at pH 8.5) eluted at 0.06 to 0.18 M KCl. CEL I (more active at pH 5.5) eluted at 0.12 to 0.22 M KCl. Narrow peak fractions of CEL II activity were pooled to avoid protein contaminants from lower concentrations of KCl and to avoid CEL I (fractions 0.09 to 0.15 M KCl) from the higher concentrations of KCl. CEL I was pooled between 0.15 and 0.21 M KCl.

The CEL I pool was dialyzed overnight against 2 Liters of Buffer A containing 100 µM PMSF and stored at 4° C. until it was further purified.

The CEL II pool was dialyzed overnight against 2 Liters of Buffer C (10 mM PIPES-NaOH, pH 7.2, 5 mM α-methyl-mannoside, 0.01% TRITON™ X-100) containing 100 µM PMSF in preparation for Mono S chromatography.

Mono S HR 5/5 Chromatography of CEL II (Final). To the dialyzed CEL II pool in Buffer C was added 1 M α-methyl-mannoside to a final concentration of 50 mM in α-methyl-mannoside. The pH of the resulting sample was adjusted to 6.2 by the addition of 1 M PIPES (pH 6.0) (~2 mL). The sample was loaded onto a 1-mL Mono S HR 5/5 column equilibrated in Buffer D (50 mM PIPES-NaOH, pH 6.2, 5 mM α-methyl-mannoside, 0.01% TRITON™ X-100) containing 45 mM α-methyl-mannoside and 100 µM PMSF at 0.5 mL/minute. The column was washed with 5 mL of Buffer D containing 45 mM α-methyl-mannoside and 100 µM PMSF at 1 mL/minute. CEL nucleases were eluted with a 25-mL linear gradient of 0 to 0.3 M KCl in Buffer D containing 45 mM α-methyl-mannoside and 100 µM PMSF at 1 mL/minute with 0.5 mL/fraction. Assays were conducted at pH 5.5 and 8.5. The major peak of protein contaminants eluted at 0.05 to 0.21 M KCl. CEL I eluted at 0.15 to 0.22 M KCl. CEL II eluted at 0.18 to 0.28 M KCl. CEL II activity were pooled from 0.21 and 0.26 M KCl fractions, thereby avoiding protein contaminants and CEL I. After pooling, the pH was immediately adjusted to pH 8.0 by the addition of 1 M Tris-HCl (pH 8.0); approximately 0.5 mL of Tris was added to 3–3.5 mL of pooled enzyme.

The CEL II pool was dialyzed overnight against 1 Liter of Buffer A containing 100 µM PMSF.

Mono Q HR 5/5 Chromatography of CEL II (Final). To the dialyzed CEL II pool from the Mono S column was added α-methyl-mannoside to a final concentration of 50 mM. The sample was loaded onto a Mono Q HR 5/5 column equilibrated in Buffer A containing 45 mM α-methyl-mannoside at 0.5 mL/minute. The column was washed with 5 mL of Buffer A containing 45 mM α-methyl-mannoside at 1 mL/minute. CEL II was eluted with a 25-mL linear gradient of 0 to 0.3 M KCl in Buffer A containing 45 mM α-methyl-mannoside at 1 mL/minute with 0.5 mL/fraction. Assays were conducted at pH 8.5. CEL II eluted between 0.1 and 0.25 M KCl. Narrow fractions of CEL II activity were pooled to avoid protein contaminants that elute at higher and lower concentrations of KCl. CEL II was pooled from fractions between 0.1 and 0.18 M KCl.

The CEL II pool was dialyzed overnight against 1 Liter of Storage Buffer (50 mM Tris-HCl, pH 7.5, 100 mM KCl, 10 µM ZnCl$_2$, 0.01% TRITON™ X-100, 50% glycerol) and stored at −20° C.

Dialysis of CEL I Against Buffer C (Final). The CEL I Heparin SEPHAROSE® pool stored in Buffer A at 4° C. was dialyzed overnight against 2 Liters of Buffer C containing 100 µM PMSF before HITRAPT™ Heparin HP chromatography.

HITRA™ Heparin HP Chromatography of CEL I (Final). To the dialyzed Heparin SEPHAROSE® CEL I pool was added α-methyl-mannoside to a final concentration of 50 mM. The pH of the resulting sample was adjusted to 6.2 by the addition 1 M PIPES (pH 6.0) (~2 mL). The sample was loaded unto a 1-mL HiTrap Heparin HP column equilibrated in Buffer D containing 45 mM α-methyl-mannoside at 0.5 mL/minute. The column was washed with 5 mL of Buffer D containing 45 mM α-methyl-mannoside at 1 mL/minute. CEL I was eluted with a 20-mL linear gradient of 0 to 0.5 M KCl in Buffer D containing 45 mM α-methyl-mannoside at 1 mL/minute with 0.5 mL/fraction. Assays were conducted at pH 5.5. The major protein contamination peak eluted between 0.1 and 0.38 M KCl. CEL I eluted between 0.32 and 0.47 M KCl. Narrow fractions of CEL I activity were pooled to avoid the protein contaminants that eluted at lower concentrations of KCl between 0.35 and 0.45 M KCl. After pooling, the pH was immediately adjusted to pH 8.0 by the addition of 1 M Tris-HCl (pH 8.0); approximately ~0.5 mL of Tris was added to 3–3.5 mL of pooled enzyme.

The CEL I pool was dialyzed overnight against 1 Liter of Buffer A containing 100 µM PMSF.

Mono Q HR 5/5 Chromatography of CEL I (Final). To the dialyzed CEL I pool from HITRAP™ Heparin HP was added α-methyl-mannoside to a final concentration of 50 mM. The resulting sample was loaded onto a Mono Q HR 5/5 column equilibrated in Buffer A containing 45 mM α-methyl-mannoside at 0.5 mL/minute.

The column was washed with 5 mL of Buffer A containing 45 mM α-methyl-mannoside at 1 mL/minute. CEL I was eluted with a 25-mL linear gradient of 0 to 0.3 M KCl in Buffer A containing 45 mM α-methyl-mannoside at 1 mL/minute with 0.5 mL/fraction. Fractions were assayed at pH 5.5. CEL I eluted between 0.09 and 0.15 M KCl. The peak fractions of CEL I activity were pooled between 0.11 to 0.13 M KCl.

The CEL I pool was dialyzed overnight against Storage Buffer and stored at −20° C.

Recovery of CEL I and CEL II (Final). The purification of CEL I and CEL II was monitored by carrying out unit and protein determinations on pools from each purification step. The results of such monitoring are shown in Table 4, which shows typical yield and fold-purification results from the purification at each step. In addition, graphs were plotted for each chromatography step in order to make informed pooling decisions. These graphs showed profiles for protein concentration, unit activity at pH 5.5 and 8.5, and salt concentration.

TABLE 4

| Fraction | Volume (mL) | Protein Conc. (mg/mL) | Total Protein (mg) | Unit Activity (Units/mL)[a] |
|---|---|---|---|---|
| Clarified Crude | 6750 | 7.8 | 52620 | 53,000 (53,000) |
| (NH$_4$)$_2$SO$_4$ | 775 | 8.9 | 6898 | 118,000 (75,000) |
| Con A SEPHAROSE ® | 650 | 0.41 | 267 | 53,000 (21,000) |
| Q SEPHAROSE ® | 195 | 0.43 | 84 | 45,000 (38,000) |
| Heparin SEPHAROSE ® CEL I | 36 | 0.037 | 1.33 | 69,000 (45,000) |
| Heparin SEPHAROSE ® #2 CEL I | 2.9 | 0.0125 | 0.136 | 270,000 (170,000) |
| Mono Q CEL I | 3.5 | 0.001 | 0.0035 | 50,000 (70,000) |
| Mono Q Concentration CEL I[b] | 0.9 | 0.0039 | 0.0035 | 380,000 (250,000) |
| Heparin SEPHAROSE ® CEL II | 39 | 0.077 | 3.0 | 21,000 (72,000) |

TABLE 4-continued

| Fraction | | | | |
|---|---|---|---|---|
| Mono S CEL II | 3.4 | 0.015 | 0.051 | 65,000 (360,000) |
| Mono Q CEL II | 5.5 | 0.001 | 0.0055 | 8,000 (83,000) |
| Mono Q Concentration CEL II[c] | 1.35 | 0.004 | 0.0055 | 21,000 (230,000) |

| Fraction | Total Activity × $10^5$ (Units) | Specific Activity (Units/mg) | Fold Purification | % Recovery |
|---|---|---|---|---|
| Clarified Crude | 3580 (3580) | 6,800 (6,800) | 1 (1) | 100 (100) |
| $(NH_4)_2SO_4$ | 1150 (580) | 13,192 (8,408) | 1.9 (1.2) | 25 (16) |
| Con A SEPHAROSE ® | 345 (137) | 129,213 (51,310) | 19 (7.5) | 9.6 (3.8) |
| Q SEPHAROSE ® | 88 (74) | 104,760 (88,095) | 15.4 (13.0) | 2.4 (2.1) |
| Heparin SEPHAROSE ® CEL I | 25 (16) | 1,879,700 (1,203,010) | 276 (177) | 0.69 (0.45) |
| Heparin SEPHAROSE ® #2 CEL I | 7.8 (4.9) | 21,750,000 (13,694,440) | 3,199 (2,014) | 0.22 (0.14) |
| Mono Q CEL I | 1.75 (2.45) | 50,000,000 (70,000,000) | 7,353 (10,294) | 0.05 (0.07) |
| Mono Q Concentration CEL I[b] | 3.4 (2.25) | 97,714,430 (64,285,710) | 14,370 (9,453) | 0.1 (0.06) |
| Heparin SEPHAROSE ® CEL II | 8.2 (28) | 273,330 (933,330) | 40.1 (137) | 0.23 (0.78) |
| Mono S CEL II | 2.2 (12.2) | 433,330 (24,000,000) | 64 (3,529) | 0.06 (0.34) |
| Mono Q CEL II | 0.4 (4.6) | 8,000,000 (83,636,360) | 1,176 (12,299) | 0.012 (0.13) |
| Mono Q Concentration CEL II[c] | 0.3 (3.1) | 5,163,600 (56,454,550) | 759 (8,302) | 0.008 (0.09) |

[a]Solubilization units without parenthesis were determined at pH 5.5 and with parenthesis at pH 8.5.
[b]CEL I was 80% homogeneous as determined by visual inspection (see FIG. 4).
[c]CEL II was 25% homogeneous as determined by visual inspection (see FIG. 4).

EXAMPLE 4

Amino Acid Sequence Determination

CEL II nuclease (Mono Q Concentrated Pool; Table 4) was buffer exchanged into Dilution Buffer (25 mM Tris-HCl, pH 7.5, 100 mM KCl, 10 μM $ZnCl_2$) and concentrated using a MICROCON® YM-10 concentrator (MILLIPORE®, Billerica, Mass.). The sample was centrifuged in the concentrator at 12,000 rpm in an EPPENDORF 5415D microfuge at 4° C. The concentrated protein was precipitated by adding an equal volume of cold 30% TCA and allowing the tube sit on ice for 30 minutes. The sample was centrifuged at 12,000 rpm at 4° C. for 10 minutes, the supernatant was discarded, and the pellet was washed with cold acetone. The pellet obtained after centrifugation was air-dried and dissolved in SDS-PAGE sample buffer containing β-mercaptoethanol. The sample was electrophoresed on a 14% Tris-glycine gel (INVITROGEN™). Proteins were then electro-transferred onto a PVDF membrane at 25 volts (constant voltage) for one hour using 1×Electroblot Buffer (10 mM CAPS, pH 11.0, 10% methanol). The membrane was stained in 0.1% Ponceau S (SIGMA, St. Louis, Mo.) for 5 minutes and subsequently de-stained in 1% acetic acid. CEL II in the presence of a reducing agent separates into two fragments at 14 kDa and 28 kDa (FIG. 4). Sections of the PVDF membrane containing each of these bands were cut out and amino terminal amino acid sequence analysis was performed.

What is claimed is:

1. A purified and isolated CEL II endonuclease protein having a specific activity of greater than 10,000,000 units per mg protein as determined by DNA solubilization at pH 8.5 or CEL I endonuclease protein having a specific activity of greater than 96,000,000 units per mg protein as determined by DNA solubilization at pH 5.5.

2. The isolated CEL II endonuclease of claim 1, wherein said CEL II endonuclease is substantially free of CEL I endonuclease.

3. The isolated CEL I endonuclease of claim 1, wherein said CEL I endonuclease is substantially free of CEL II endonuclease.

4. A method for preparing an isolated CEL I or CEL II endonuclease protein of claim 1 comprising:
   a) extracting proteins from a sample;
   b) separating the proteins by concanavalin A affinity chromatography;
   c) separating the product of step (b) by anion exchange chromatography; and d) separating the product of step (c) by Heparin affinity chromatography so that a CEL I or CEL II protein is isolated.

5. The method of claim 4, further comprising separating the product of step (d) by one or more Heparin affinity chromatography steps.

6. The method of claim 4, wherein the sample is of plant origin.

7. The method of claim 6, wherein the plant is celery.

8. A method for separating CEL I and CEL II in a mixture comprising subjecting a mixture containing CEL I and CEL II to heparin affinity chromatography so that CEL I and CEL II are separated.

9. A composition comprising the isolated CEL II or CEL I endonuclease of claim 1.

* * * * *